United States Patent
Okada et al.

(10) Patent No.: US 10,232,176 B2
(45) Date of Patent: Mar. 19, 2019

(54) BIOLOGICAL SIGNAL DISPLAY APPARATUS

(75) Inventors: Munehito Okada, Tokyo (JP); Hitoshi Sano, Tokyo (JP); Tetsuro Tatsuoka, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1537 days.

(21) Appl. No.: 13/267,304

(22) Filed: Oct. 6, 2011

(65) Prior Publication Data
US 2012/0089044 A1     Apr. 12, 2012

(30) Foreign Application Priority Data
Oct. 8, 2010  (JP) ................................ 2010-228903

(51) Int. Cl.
| | | |
|---|---|---|
| A61B 5/00 | (2006.01) | |
| A61B 5/0484 | (2006.01) | |
| A61B 5/0488 | (2006.01) | |
| A61B 5/044 | (2006.01) | |
| A61N 1/36 | (2006.01) | |
| A61N 1/08 | (2006.01) | |
| A61N 1/372 | (2006.01) | |

(52) U.S. Cl.
CPC .......... *A61N 1/36014* (2013.01); *A61N 1/08* (2013.01); *A61B 5/044* (2013.01); *A61B 5/0484* (2013.01); *A61B 5/0488* (2013.01); *A61B 5/4821* (2013.01); *A61B 5/743* (2013.01); *A61N 1/37247* (2013.01)

(58) Field of Classification Search
CPC .................................................... A61B 5/0484
USPC ........................................................ 600/544
See application file for complete search history.

(56) References Cited

U.S. PATENT DOCUMENTS

| | | | | |
|---|---|---|---|---|
| 5,406,957 A | * | 4/1995 | Tansey .......................... | 600/545 |
| 6,002,960 A | * | 12/1999 | Sternberger et al. ......... | 600/546 |
| 6,067,467 A | * | 5/2000 | John ............................. | 600/544 |
| 6,224,549 B1 | | 5/2001 | Drongelen | |

(Continued)

FOREIGN PATENT DOCUMENTS

| | | |
|---|---|---|
| GB | 2113846 A | 8/1983 |
| JP | 58-133233 A | 8/1983 |

(Continued)

OTHER PUBLICATIONS

Extended European Search Report, dated Jan. 30, 2012, issued by the European Patent Office in corresponding European Application No. 11184245.6.

(Continued)

*Primary Examiner* — Sean P Dougherty
(74) *Attorney, Agent, or Firm* — Sughrue Mion, PLLC (57) ABSTRACT

A biological signal display apparatus includes: a stimulation unit which performs stimulation on a living body; a measurement unit which measures an evoked response evoked by the stimulation; a calculator which calculates a feature amount of the evoked response; a display unit; and a display controller which, based on the feature amount calculated by the calculator, displays a bar-shaped image on the display unit, each time when the stimulation is performed, the bar-shaped image corresponding with the evoked response on the display unit.

10 Claims, 5 Drawing Sheets

(56) References Cited

U.S. PATENT DOCUMENTS

| | | | |
|---|---|---|---|
| 6,322,516 B1 * | 11/2001 | Masuda | A61B 5/021 600/490 |
| 7,120,486 B2 * | 10/2006 | Leuthardt et al. | 600/545 |
| 8,255,045 B2 * | 8/2012 | Gharib et al. | 600/547 |
| 8,568,331 B2 * | 10/2013 | Bertagnoli et al. | 600/554 |
| 2003/0018242 A1 * | 1/2003 | Hursh et al. | 600/300 |
| 2003/0083708 A1 * | 5/2003 | Bradley | A61N 1/3712 607/27 |
| 2004/0193068 A1 * | 9/2004 | Burton et al. | 600/544 |
| 2005/0154329 A1 * | 7/2005 | Shimazu et al. | 600/554 |
| 2009/0018610 A1 | 1/2009 | Gharib et al. | |
| 2009/0054804 A1 * | 2/2009 | Gharib et al. | 600/554 |
| 2009/0105604 A1 * | 4/2009 | Bertagnoli et al. | 600/546 |
| 2010/0076333 A9 * | 3/2010 | Burton et al. | 600/544 |
| 2010/0249638 A1 * | 9/2010 | Liley | 600/544 |
| 2010/0305646 A1 * | 12/2010 | Schulte | A61B 5/04525 607/18 |
| 2011/0125046 A1 * | 5/2011 | Burton et al. | 600/544 |
| 2011/0282230 A9 * | 11/2011 | Liley | 600/544 |

FOREIGN PATENT DOCUMENTS

| | | |
|---|---|---|
| JP | 59-121387 A | 7/1984 |
| JP | 10-057331 A | 3/1998 |
| JP | 2002-541891 A | 12/2002 |
| JP | 2007-135716 A | 6/2007 |

OTHER PUBLICATIONS

Communication, dated Nov. 23, 2012, issued by the European Patent Office in counterpart European Application No. 11184245.6.

Office Action dated Mar. 10, 2014 issued by the Japanese Patent Office in counterpart Japanese Patent Application No. 2010-228903.

Office Action, dated Oct. 28, 2013, issued by the Japanese Patent Office, in counterpart Application No. 2010-228903.

* cited by examiner

BIOLOGICAL SIGNAL DISPLAY APPARATUS

BACKGROUND OF THE INVENTION

The present invention relates to a biological signal display apparatus which displays an evoked response that is elicited by stimulating a living body, in an easily understandable and adequate manner. A situation where an evoked response has an abnormal value or the waveform is not reproducible indicates that a change or abnormality occurs in the living body, and hence it is possible to know the state of the living body rapidly and easily.

In a related-art apparatus, it is usual that a waveform obtained by a measurement is displayed as it is, or that the amplitude, latency, and the like, which are feature amounts of the waveform, are displayed as numerical values.

When such a related-art display is performed, the doctor performing surgery is apart from the related-art apparatus, and cannot operate the apparatus. Therefore, the doctor must approach the vicinity of the apparatus to gaze the waveform on the display, or ask a medical staff to read out the values of the latency, the amplitude, etc on the display. In order to enable the usefulness of an evoked response to be exerted during surgery, consequently, considerable effort is required. In an evoked response, particularly, its change must be recognized at each time of stimulation. Therefore, such a related-art display is not adequate for monitoring a patient during surgery.

In the viewpoint of intuitive grasping of the state of a biological signal, there are an electrocardiograph in which the local maximum value of an electrocardiographic signal is displayed in bar graph form (see JP-A-10-057331), and a sphygmomanometer in which the blood pressure is displayed in the form of a bar (see JP-A-2007-135716). However, the apparatus disclosed in JP-A-10-057331 is intended to check the connection state of electrodes, and the apparatus disclosed in JP-A-2007-135716 simulates the display of a cuff pressure in blood pressure measurement by a mercury column. Even when these techniques are applied as they are to a display of an evoked response obtained by stimulation, therefore, they are not useful.

SUMMARY

It is therefore an object of the invention to provide a biological signal display apparatus which can display an evoked response in an easily understandable manner.

In order to achieve the object, according to the invention, there is provided a biological signal display apparatus comprising: a stimulation unit which performs stimulation on a living body; a measurement unit which measures an evoked response evoked by the stimulation; a calculator which calculates a feature amount of the evoked response; a display unit; and a display controller which, based on the feature amount calculated by the calculator, displays a bar-shaped image on the display unit, each time when the stimulation is performed, the bar-shaped image corresponding with the evoked response on the display unit.

On the display unit, the feature amount may be set to one of an abscissa and an ordinate, and the evoked response may be set to another one of the abscissa and the ordinate.

The display controller may display and hold at least one of a maximum value of the feature amount and a minimum value of the feature amount and a value of the feature amount based on last stimulation.

The stimulation may include a first stimulation and a second stimulation that is performed after the first stimulation is performed. When the second stimulation is performed, the display controller may delete the bar-shaped image that is displayed at a time when the first stimulation is performed.

The evoked response may include a first evoked response and a second evoked response which are different in kind from each other.

The evoked response may include at least one of a somatosensory evoked potential, an auditory evoked potential, a visual evoked potential, and an evoked electromyogram.

The stimulation may include at least one of electric stimulation, acoustic stimulation, and optical stimulation.

The display controller may display, on the display unit, a numerical value corresponding to the stimulation performed by the stimulation unit.

The feature amount may include at least one of an amplitude, area, and latency of a signal of the evoked response.

The biological signal display apparatus may further comprise an external outputting unit which outputs an image to be displayed on the display unit, in a manner in which the image can be displayed on an external apparatus.

DETAILED DESCRIPTION OF EMBODIMENTS

Figure 1:
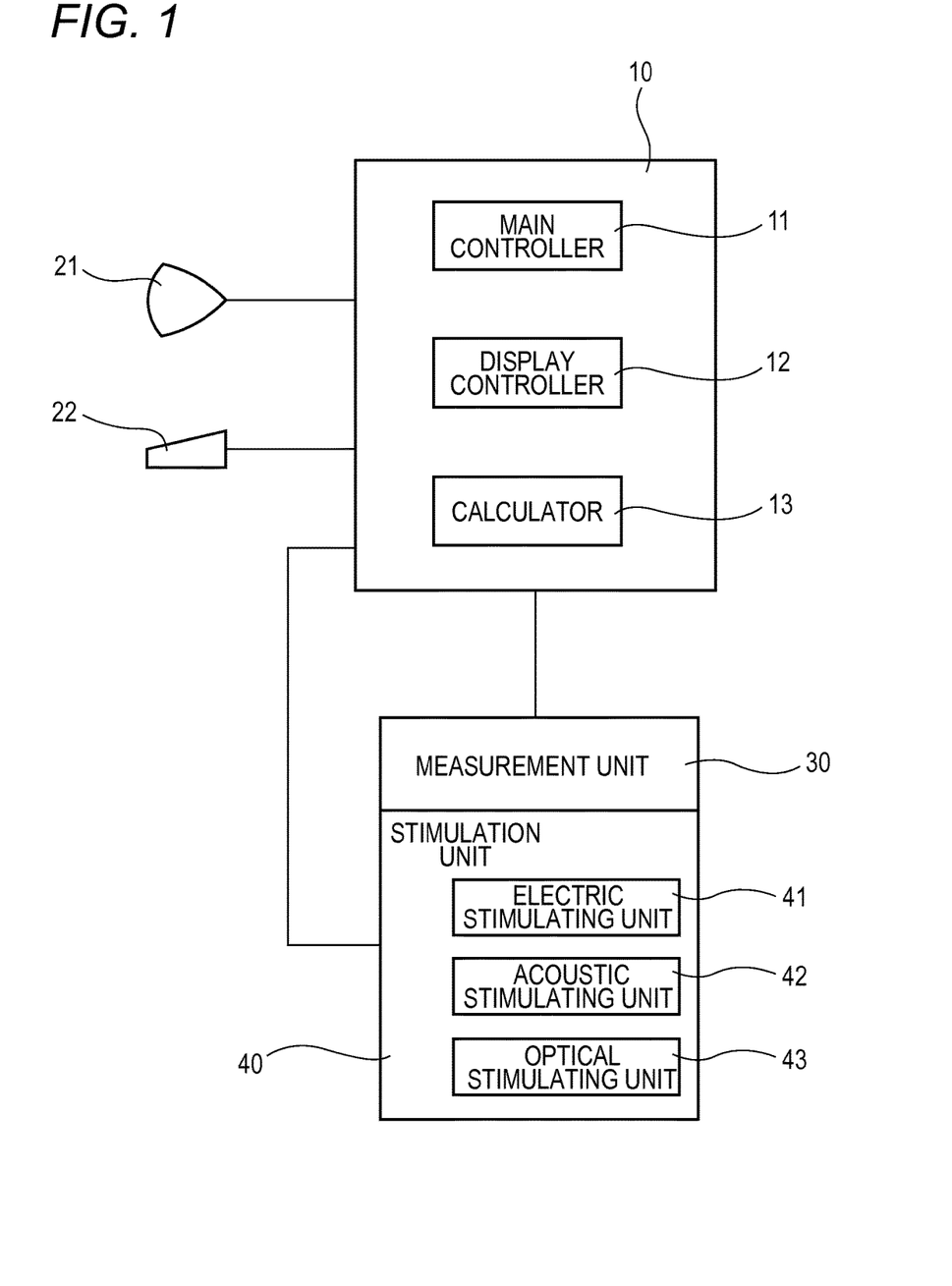
FIG. 1 is a block diagram showing the configuration of an embodiment of the biological signal display apparatus of the invention.

Hereinafter, an embodiment of the biological signal display apparatus of the invention will be described with reference to the accompanying drawings. In the figures, the identical components are denoted by the same reference numerals, and duplicated description will be omitted. FIG. 1 shows a diagram of the embodiment of the biological signal display apparatus. The biological signal display apparatus includes a body unit 10 configured by a computer, a display unit 21 configured by an LCD or LEDs, an input unit 22 configured by a mouse, a touch panel, a keyboard, and the like, a measurement unit 30, and a stimulation unit 40.

The stimulation unit 40 is requested to perform at least one of electric stimulation, acoustic stimulation, and optical stimulation. In the embodiment, the stimulation unit 40 includes an electric stimulating unit 41, an acoustic stimulating unit 42, and an optical stimulating unit 43. Electrodes which are not shown are connected to the electric stimulating unit 41, and, when a desired voltage is applied to the electrodes, stimulation is performed. Under the control of a main controller 11 of the body unit 10, the stimulation unit 40 generates stimulation.

The measurement unit 30 which is connected to the stimulation unit 40 measures at least one or more evoked responses which are evoked by stimulation. Examples of the evoked responses include at least one of a somatosensory evoked potential, an auditory evoked potential, a visual evoked potential, an evoked electromyogram, and the like. Alternatively, the measurement unit may measure an evoked response other than the above.

A signal of the evoked response measured by the measurement unit 30 is sent to the body unit 10 connected thereto. The body unit 10 includes: the main controller 11 which functions as a computer to process the whole; a display controller 12 which performs a display control such as production of an image to be displayed on the display unit 21; and a calculator 13.

Figure 2:
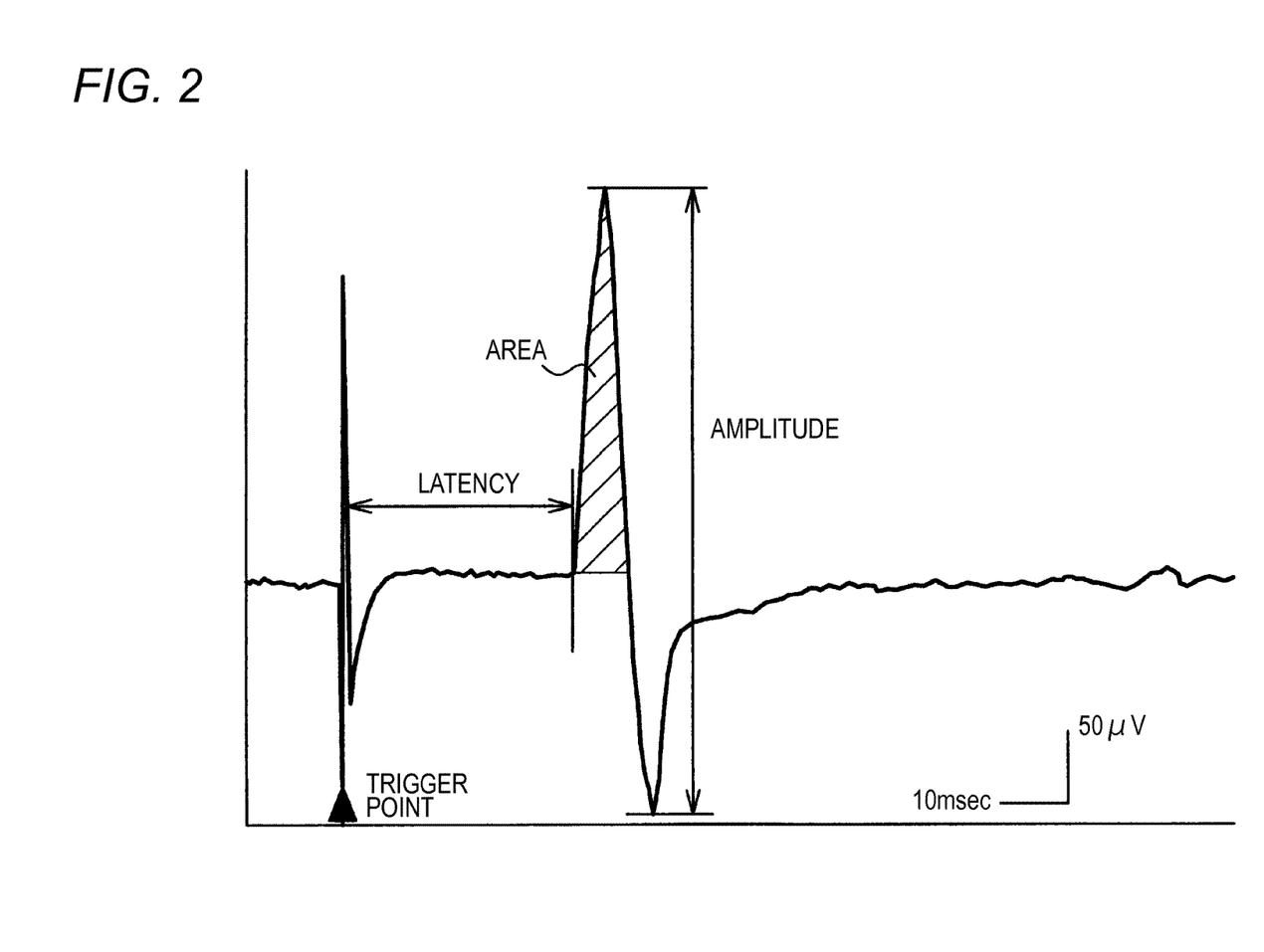
FIG. 2 is a waveform chart illustrating a waveform example and feature amounts measured by the embodiment of the biological signal display apparatus of the invention.

The calculator 13 receives the evoked response signal sent from the measurement unit 30, and calculates the feature amount of the evoked response. For example, the evoked response signal has a shape shown in FIG. 2, and the feature amount is the amplitude, the area, the latency, or the like, and may contain at least one of them. In the waveform of FIG. 2, the amplitude, the latency, and the area are shown as feature amounts.

Figure 3:
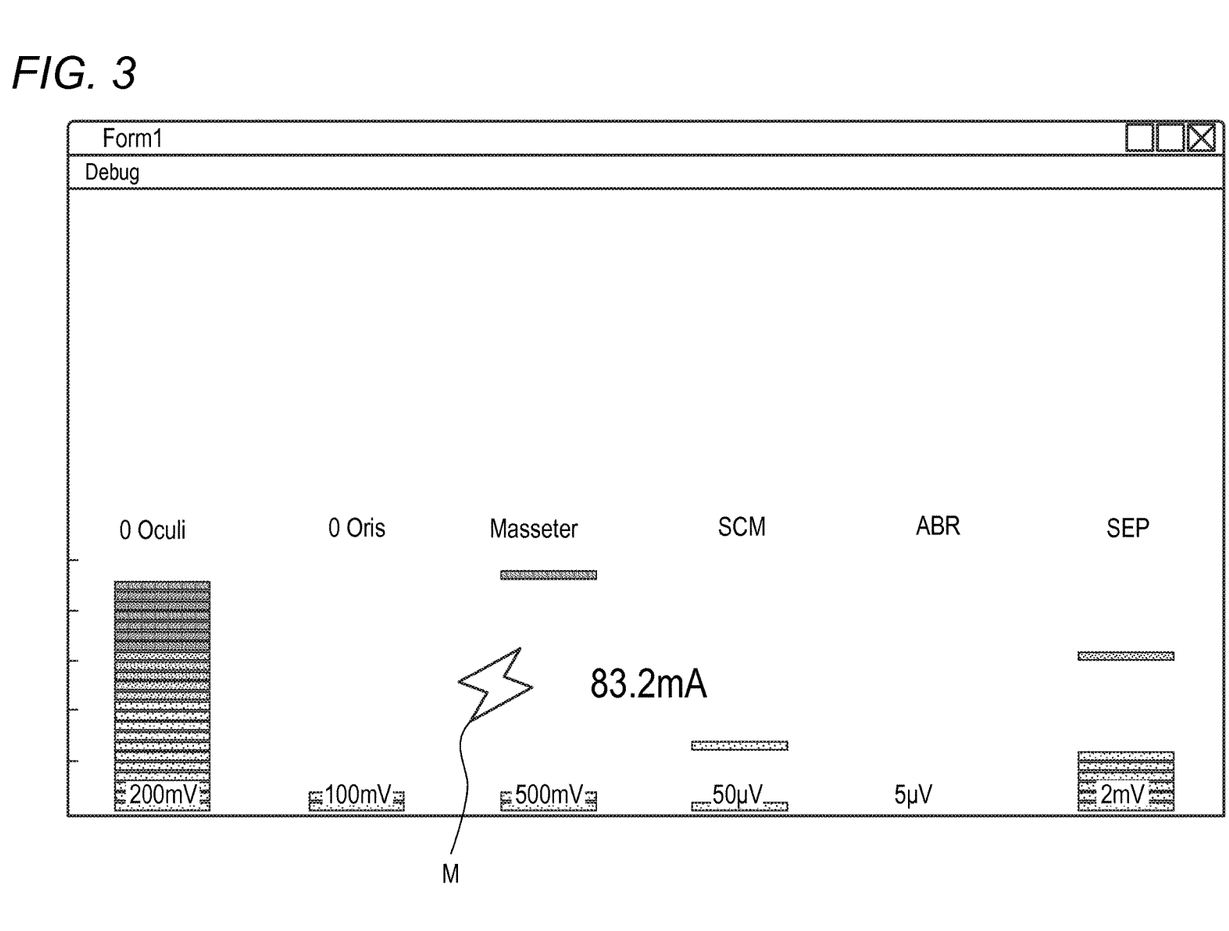
FIG. 3 is a view showing an example of a screen displayed by the embodiment of the biological signal display apparatus of the invention.

The display controller 12, based on the feature amounts calculated by the calculator 13, displays bar-shaped images correspondingly with the evoked responses on the display unit 21. FIG. 3 shows a display example using bar-shaped images. In the example, a bar graph is displayed by bar-shaped images corresponded to the evoked responses, and kinds of evoked responses or O Oculi (orbicularis oculi muscle), O Oris (orbicularis oris muscle), Masseter (masseter muscle), SCM (sternocleidomastoid muscle), ABR (auditory brainstem response), and SEP (somatosensory evoked potential) are arranged with starting from the left side on the abscissa. Correspondingly with the kinds of evoked responses, bar-shaped images having a length corresponding to the degree of a feature amount are displayed. FIG. 3 shows the screen example in which the evoked responses are set to the abscissa and the feature amounts are set to the ordinate. Alternatively, the evoked responses and the feature amounts may be set in the opposite manner to the ordinate and the abscissa.

Each of the bar-shaped images is configured by stacking a plurality of laterally rectangular segments, and the potential of one segment is indicated for each of the kinds of the evoked responses. With respect to the color of each segment, the lower-most position is indicated by green, yellow is further mixed as advancing upward, the middle position is indicated by yellow, red is further mixed as advancing upward, and the upper-most position is indicated by red. In the vicinity of the middle of the display of a bar-shaped image, the value (in the embodiment, the electric quantity) during stimulation is displayed together with a stimulation mark M having a lightning shape. In each feature amount, normal and abnormal ranges may be displayed by different colors.

In each of the bar graphs of O Oculi (orbicularis oculi muscle) and O Oris (orbicularis oris muscle), an evoked response which is currently measured is shown, and hence a feature amount is displayed by a series of segments. With respect to each of the other kinds of evoked responses, by contrast, the maximum value is displayed while being held by one segment, and, below the segment, the steady state value is displayed in bar graph form.

Figure 4:
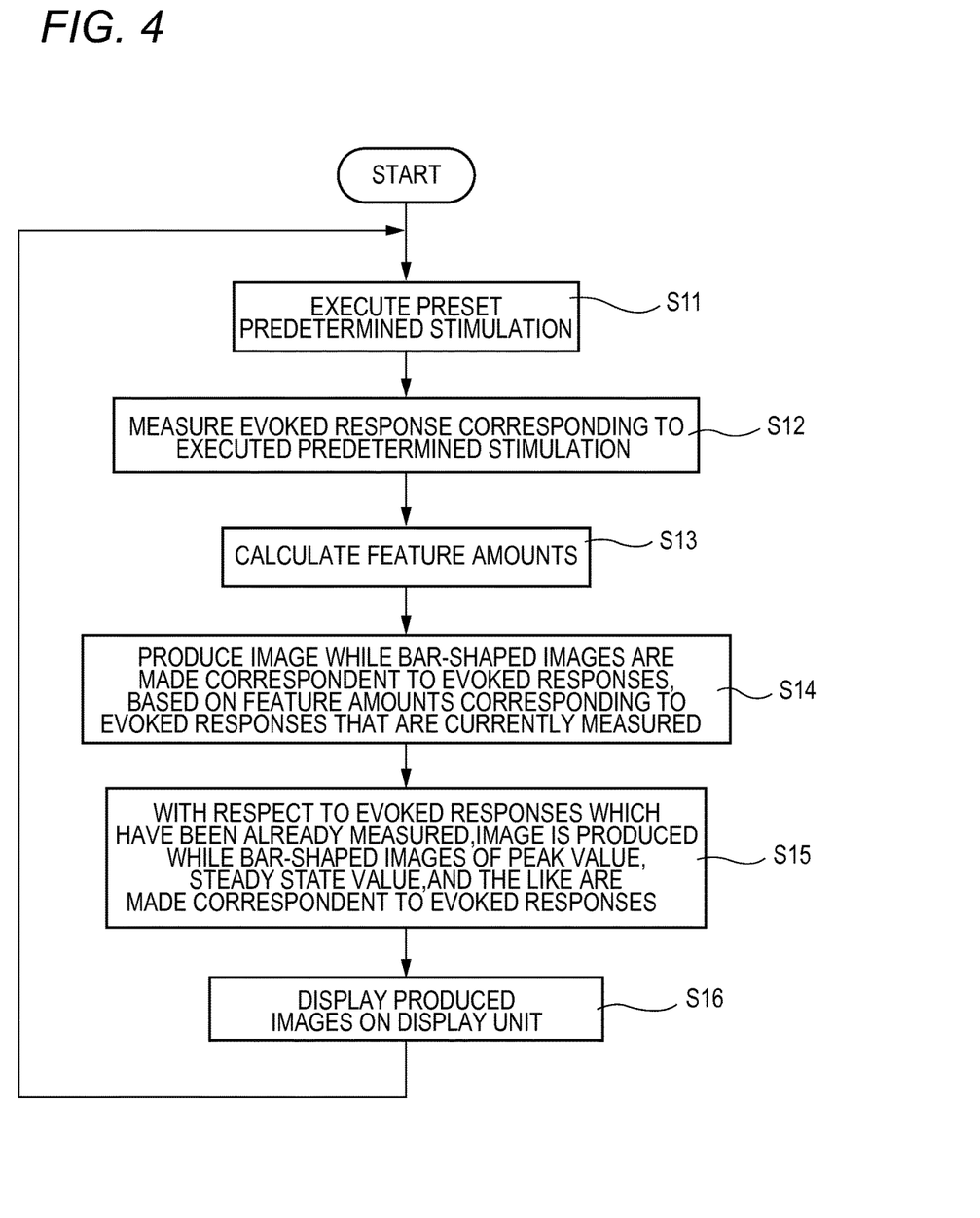
FIG. 4 is a flowchart showing an image producing operation in the embodiment of the biological signal display apparatus of the invention.

The display screen shown in FIG. 3 is produced and displayed as a result of an operation in which the main controller 11, the display controller 12, and the calculator 13 operate together with the measurement unit 30 and the stimulation unit 40 based on the flowchart shown in FIG. 4. Therefore, their operations will be described with reference to the flowchart. Before the evoked response measurement by the apparatus, the operator sets the kind of stimulation to be used, feature amounts, and the like through the input unit 22, and adequately arranges necessary equipment of the apparatus such as the electrodes.

When an operation of starting the measurement is performed, the main controller 11 instructs the stimulation unit 40 so as to execute the preset predetermined stimulation (S11). Moreover, the main controller 11 controls the measurement unit 30 so as to measure the evoked response corresponding to the predetermined stimulation which is executed by the stimulation unit 40 (S12). As a result, a signal of the measured evoked response is sent from the measurement unit 30 to the calculator 13 of the body unit 10.

The calculator 13 calculates the preset feature amounts (S13), and sends the calculation result to the display controller 12. The display controller 12 which receives the feature amounts produces an image of the bar-graph portion of FIG. 3 while bar-shaped images are made correspondent to the evoked responses, based on the feature amounts corresponding to the evoked responses that are currently measured (S14). With respect to evoked responses which have been already measured, an image of the bar-graph portion of FIG. 3 is produced while bar-shaped images of the peak value (maximum value), the steady state value, and the like are made correspondent to the evoked responses (S15). The images which are produced in steps S14 and S15 are displayed on the display unit 21 (S16), and the control returns to step S11 to continue the process. In this case, when the predetermined stimulation is newly executed (S11), preferably, the bar-shaped image which has been already displayed by the past stimulation may be deleted, and a bar-shaped image based on the feature amount due to the new stimulation may be displayed.

Figure 5:
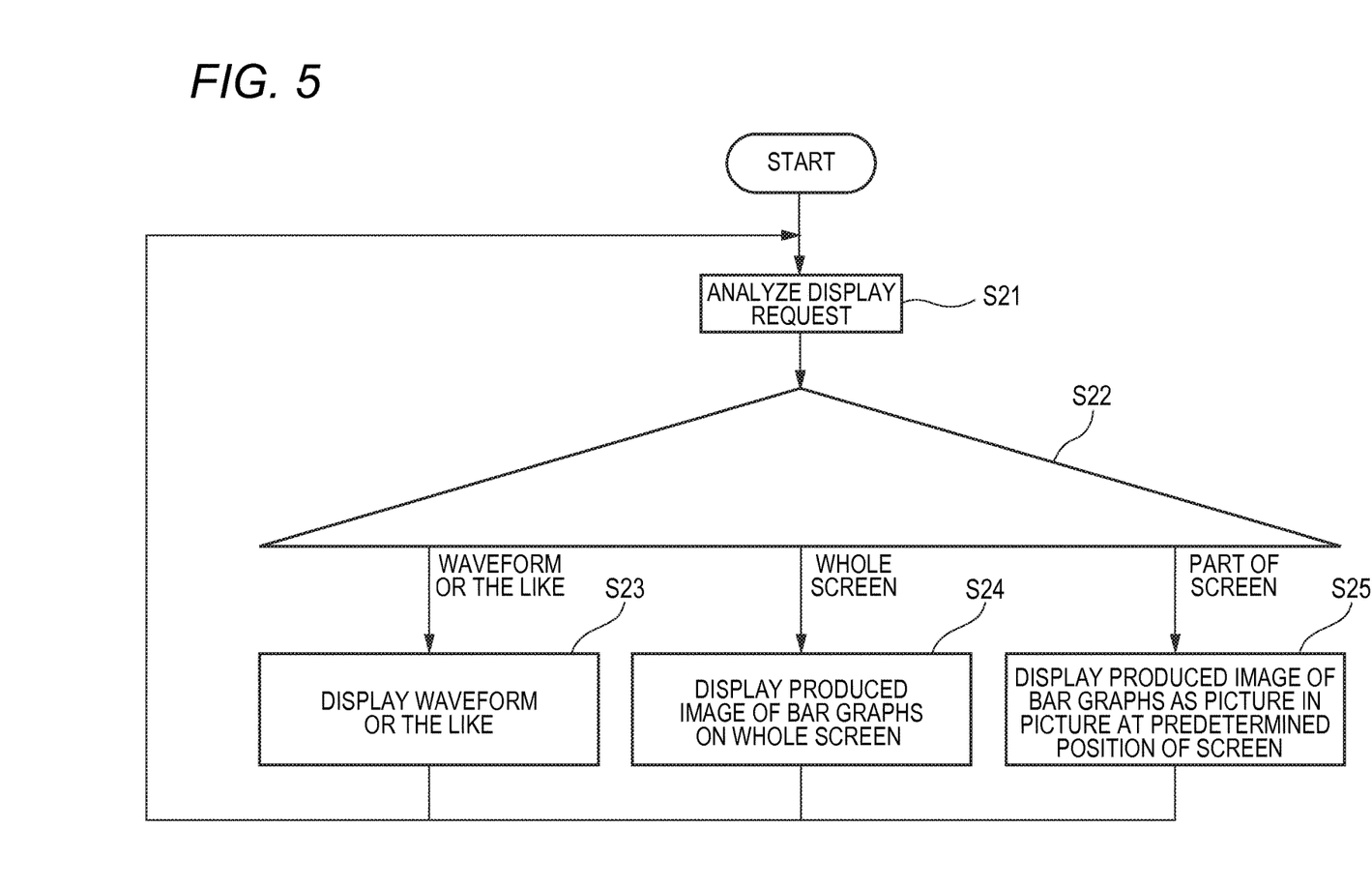
FIG. 5 is a flowchart showing an image switching operation in the embodiment of the biological signal display apparatus of the invention.

On the other hand, the main controller 11 obtains a display request which is input by the operator, and performs a control shown in FIG. 5 to switch screens. Namely, the main controller obtains a display request which is input by the operator, analyzes the request (S21), and detects whether the request requests a display of a waveform or the like, that on the whole screen, or that on a part of the screen (S22).

If it is detected that the request requests a display of a waveform or the like, an evoked response is displayed (S23). If it is detected in step S22 that the request requests a display on the whole screen, an image of bar graphs which is produced as shown in, for example, FIG. 3 is displayed on the whole screen (S24). The biological signal display apparatus of the embodiment may further include an external outputting unit which outputs the image to be displayed on the display unit, in a manner in which the image can be displayed on an external apparatus. In this case, when a display request is issued by an external apparatus such as a display apparatus disposed in a surgery room, eyeglasses or goggles worn by the doctor performing surgery, or a microscope, or when a display on an external apparatus is enabled, information corresponding to the display request may be output through the external outputting unit. At least one of the feature amounts calculated by the calculator 13 in correspondence with the stimulation performed in the stimulation unit 40 may be displayed on the display unit 21 and/or output through the external outputting unit.

As described above, the displayed screen configured by bar graphs of evoked responses is obvious at a glance. Therefore, the doctor performing surgery can intuitively know the state of the patient without stopping the operation, and without bothering another medical staff. Therefore, the apparatus is expected to be very useful when the surgery is to be adequately performed.

According to an aspect of the invention, at least one or more evoked responses which are evoked by stimulation are measured, feature amounts of the evoked responses are calculated, and, based on the calculated feature amounts, bar-shaped images are displayed correspondingly with the feature amounts, on the display unit. Therefore, the evoked responses can be displayed in an easily understandable and adequate manner.

According to an aspect of the invention, the display is performed while the feature amounts are set to one of the abscissa and the ordinate, and bar-shaped images are set to the other one of the abscissa and the ordinate. In accordance with the display region, therefore, bar-shaped images can be displayed vertically or horizontally.

According to an aspect of the invention, at least one of the maximum and minimum values of the feature amounts, and the values of the previous stimulation is displayed while being held. Therefore, the value can be easily compared with that functioning as an index (for example, the normal value, the control value, and the value due to stimulation on another portion) or the like.

According to an aspect of the invention, each time when new stimulation is performed, bar-shaped images which are displayed in response to past stimulation are deleted. Therefore, it is possible to always know a response evoked by latest stimulation.

According to an aspect of the invention, the biological signal display apparatus includes the external outputting unit. Therefore, a display can be performed as Picture in Picture on eyeglasses or goggles worn by the doctor performing surgery, a microscope, or the like, and it is not necessary to approach the vicinity of a display apparatus to gaze the waveform, or to ask a medical staff to read out the values of the latency, the amplitude, etc. The working efficiency is remarkably improved.

What is claimed is:

1. A biological signal display apparatus comprising:
   a stimulator configured to stimulate a living body;
   a display; and
   at least one central processing unit configured to:
   control the stimulator to sequentially apply stimuli to the living body, the sequentially applied stimuli having a predetermined value;
   receive evoked signals of evoked responses to the sequentially applied stimuli;
   analyze the evoked signals to determine values of the evoked responses; and
   control the display to maintain on the display a bar graph of laterally rectangular bar-shaped images corresponding to the evoked responses, the laterally rectangular bar-shaped images disposed in vertically arranged columns along an abscissa of the bar graph and heights of the vertically arranged columns of laterally rectangular bar-shaped images along an ordinate of the bar graph corresponding to values of the evoked responses, a first vertically arranged column among the vertically arranged columns of laterally rectangular bar-shaped images comprising:
   a first laterally rectangular bar-shaped image corresponding to a maximum value of the evoked responses, the first laterally rectangular bar-shaped image including a first side of a first length, along the abscissa of the bar graph, and
   the first laterally rectangular bar-shaped image including a second side of a second length smaller than the first length, along the ordinate of the bar graph; and
   a second laterally rectangular bar-shaped image corresponding to a present value of a current evoked response to stimuli most recently applied to the living body,
   wherein the first laterally rectangular bar-shaped image and the second laterally rectangular bar-shaped image are simultaneously displayed in the first vertically arranged column,
   wherein the first laterally rectangular bar-shaped image and the second laterally rectangular bar-shaped image are vertically stacked in the first vertically arranged column such that the second laterally rectangular bar-shaped image is displayed below the first laterally rectangular bar-shaped image along the ordinate of the bar graph, and
   wherein the first laterally rectangular bar-shaped image and the second laterally rectangular bar-shaped image include the same coordinates along the abscissa of the bar graph;
   wherein the at least one central processing unit is further configured to control the display to display a second vertically arranged column, among the vertically arranged columns of laterally rectangular bar-shaped images, adjacent to the first vertically arranged column along the abscissa of the bar graph.

2. The biological signal display apparatus according to claim 1, wherein the at least one central processing unit is further configured to control the display to update the first laterally rectangular bar-shaped image and the second laterally rectangular bar-shaped image based on the values of the evoked responses.

3. The biological signal display apparatus according to claim 1, wherein the evoked responses are one of a somatosensory evoked potential, an auditory evoked potential, a visual evoked potential, and an evoked electromyogram.

4. The biological signal display apparatus according to claim 1, wherein the stimulator is configured to perform one of electric stimulation of an electric stimulator, acoustic stimulation of an acoustic stimulator, and optical stimulation of an optical stimulator.

5. The biological signal display apparatus according to claim 1, wherein the at least one central processing unit is further configured to control the display to display a numerical value corresponding to the predetermined value of the stimuli applied by the stimulator.

6. The biological signal display apparatus according to claim 1, wherein the values of the evoked responses comprises at least one of an amplitude, area, and latency of the evoked signals of the evoked responses.

7. The biological signal display apparatus according to claim 1, wherein the at least one central processing unit is further configured to:
   control the display to maintain, on the display, a second vertically arranged column among the vertically arranged columns of laterally rectangular bar-shaped images; and
   control the display to display different kinds of evoked responses in the first vertically arranged column and the second vertically arranged column.

8. The biological signal display apparatus according to claim 1, wherein the first laterally rectangular bar-shaped image includes a first color that is different than a second color of the second laterally rectangular bar-shaped image.

9. The biological signal display apparatus according to claim 1, wherein the at least one central processing unit is further configured to:
- control the display to display the first laterally rectangular bar-shaped image and the second laterally rectangular bar-shaped image such that the first laterally rectangular bar-shaped image and the second laterally rectangular bar-shaped image do not include overlapping coordinates along the ordinate of the bar graph.

10. The biological signal display apparatus according to claim 1, wherein the at least one central processing unit is further configured to:
- control the display to display the first laterally rectangular bar-shaped image that corresponds to a somatosensory evoked potential; and
- control the display to display another laterally rectangular bar-shaped image in another vertically arranged column, among the vertically arranged columns, wherein the other laterally rectangular bar-shaped image corresponds to an auditory evoked potential, a visual evoked potential, or an evoked electromyogram.

* * * * *